United States Patent
Kazemi Oskooei et al.

(10) Patent No.: US 11,651,841 B2
(45) Date of Patent: May 16, 2023

(54) DRUG COMPOUND IDENTIFICATION FOR TARGET TISSUE CELLS

(71) Applicant: International Business Machines Corporation, Armonk, NY (US)

(72) Inventors: Seyed Ali Kazemi Oskooei, Zurich (CH); Matteo Manica, Zurich (CH); Maria Rodriguez Martinez, Thalwil (CH); Jannis Born, Zurich (CH)

(73) Assignee: International Business Machines Corporation, Armonk, NY (US)

( * ) Notice: Subject to any disclaimer, the term of this patent is extended or adjusted under 35 U.S.C. 154(b) by 657 days.

(21) Appl. No.: 16/685,455

(22) Filed: Nov. 15, 2019

(65) Prior Publication Data

US 2020/0365238 A1 Nov. 19, 2020

Related U.S. Application Data (63) Continuation-in-part of application No. 16/413,399, filed on May 15, 2019.

(51) Int. Cl.

| | | |
|---|---|---|
| *G16C 20/70* | (2019.01) | |
| *G06N 3/08* | (2023.01) | |
| *G16B 40/20* | (2019.01) | |
| *G16C 20/30* | (2019.01) | |
| *G16C 20/50* | (2019.01) | |
| *G06N 3/04* | (2023.01) | |

(52) U.S. Cl.
CPC .......... *G16C 20/70* (2019.02); *G06N 3/0454* (2013.01); *G06N 3/08* (2013.01); *G16B 40/20* (2019.02); *G16C 20/30* (2019.02); *G16C 20/50* (2019.02)

(58) Field of Classification Search
CPC ........ G16C 20/70; G16C 20/30; G16C 20/50; G16B 40/20; G06N 3/0454; G06N 3/08
See application file for complete search history.

(56) References Cited

U.S. PATENT DOCUMENTS

| | | | |
|---|---|---|---|
| 2014/0057798 A1 | 2/2014 | Gong et al. | |
| 2017/0193157 A1 | 7/2017 | Quirk et al. | |

FOREIGN PATENT DOCUMENTS

| | | | |
|---|---|---|---|
| CN | 107609326 A | 1/2018 | |
| WO | WO2019018780 A1 | 1/2019 | |

OTHER PUBLICATIONS

Matteo Manica et al., Protein-Targeted Drug Compound Identification Unpublished U.S. Appl. No. 17/004,104, filed Aug. 27, 2020, pp. 1-25 plus 5 sheets drawings.
Paul J. Otterstedt, List of IBM Patents or Patent Applications Treated as Related, Nov. 27, 2020, pp. 1-2.
Petrova, Innovation in the pharmaceutical industry: The process of drug discovery and development, in Innovation and marketing in the pharmaceutical industry, Springer, 2014, pp. 19-81.
Goh et al., SMILES2Vec: An Interpretable General-Purpose Deep Neural Network for Predicting Chemical Properties, ArXiv Prepr. ArXiv171202034, 2017, 8 Pages.
Chang, et al., Cancer Drug Response profile scan (CDRscan): a deep learning model that predicts drug effectiveness from cancer genomic signature, Scientific reports. Jun. 11, 2018;8(1):8857.
Oskooei et al., PaccMann: Prediction of anticancer compound sensitivity with multi-modal attention-based neural networks, arXiv:1811.06802v1 [cs.LG], Nov. 16, 2018. Grace Period Disclosure pp. 1-13.
Bahdanau et al., Neural machine translation by jointly learning to align and translate, arXiv preprint arXiv:1409.0473, 2014, 15 pages.
Vaswani et al., Attention is all you need, Advances in neural information processing systems, 2017, pp. 5998-6008.
Yang et al., Hierarchical attention networks for document classification, Proceedings of the 2016 conference of the North American chapter of the association for computational linguistics: human language technologies, Jun. 2016, pp. 1480-1489.
Schwaller, et al., Found in Translation: predicting outcomes of complex organic chemistry reactions using neural sequence-to-sequence models, Chemical science, 9(28), 2018, pp. 6091-6098. DOI: 10.1039/C8SC02339E.
Lloyd, et al., Pharma r&d annual review 2017, Available at: pharmaintelligence.informa.com/resources/product-content/pharma-rd-annual-review-2018, Accessed Jun. 25, 2018, 2017, 44 pages.
Hargrave-Thomas, et al., Serendipity in anticancer drug discovery, World journal of clinical oncology 3.1, 2012, 17 pages doi: 10.5306/wjco.v3.i1.1.
Garnett, et al., Systematic identification of genomic markers of drug sensitivity in cancer cells, Nature 483 No. 7391, 2012, pp. 570-575 (Abstract Only).
Yang et al., Genomics of Drug Sensitivity in Cancer (GDSC): a resource for therapeutic biomarker discovery in cancer cells, Nucleic acids research 41.D1, 2012, pp. D955-D961.
Barretina et al., The Cancer Cell Line Encyclopedia enables predictive modeling of anticancer drug sensitivity, Nature 483, No. 7391, 2012, pp. 603-607 (Author Manuscript).
Cancer Genome Atlas Network. Comprehensive molecular portraits of human breast tumours, Nature 490, No. 7418 (2012): 61-70.
Heiser, et al., Subtype and pathway specific responses to anticancer compounds in breast cancer, Proceedings of the National Academy of Sciences, 2012, 109(8), pp. 2724-2729.

(Continued)

*Primary Examiner* — Jerry Lin
(74) *Attorney, Agent, or Firm* — Daniel Morris; Otterstedt & Kammer PLLC (57) ABSTRACT

Provide a reinforcement learning model including an agent and a critic; the critic includes a neural network pre-trained to generate, from input biomolecular data characterizing tissue cells and input compound data defining a compound molecule, a property value for said biomolecular action of that molecule on those tissue cells. The agent includes a neural network adapted to generate the compound data in dependence on input biomolecular data. Supply biomolecular data characterizing patient tissue cells to the agent and supply that data, and the compound data generated therefrom, to the critic to obtain a property value in an iterative training process in which reward values, dependent on the property values, are used to progressively train the agent to optimize the reward value. After training the agent, supply target biomolecular data, characterizing the target tissue cells, to the agent to generate compound data corresponding to a set of drug compounds.

21 Claims, 5 Drawing Sheets

(56) References Cited

OTHER PUBLICATIONS

International Cancer Genome Consortium, International network of cancer genome projects, Nature 464, 7291, 2010, pp. 993-996.
Lamb, et al., The Connectivity Map: using gene-expression signatures to connect small molecules, genes, and disease, Science, 313(5795), 2006, pp. 1929-1935.
Shoemaker, The NCI60 human tumor cell line anticancer drug screen, Nature Reviews Cancer 6, No. 10, 2006, pp. 813-823.
Costello, et al., A community effort to assess and improve drug sensitivity prediction algorithms, Nature biotechnology 32, No. 12, 2014, pp. 1202-1214.
Geeleher, Cancer biomarker discovery is improved by accounting for variability in general levels of drug sensitivity in pre-clinical models, Genome biology 17, No. 1, 2016, 190, 11 pages.
Menden et al., Machine learning prediction of cancer cell sensitivity to drugs based on genomic and chemical properties, PLoS one vol. 8, No. 4, 2013, e61318, 10 pages.
Karelson, et al., Quantum-chemical descriptors in QSAR/QSPR studies, Chem. Rev., vol. 96, No. 3, pp. 1027-1044, 1996.
Cereto-Massague, et al., Molecular fingerprint similarity search in virtual screening, Methods 71, 2015, pp. 58-63.
Luong et al., Effective approaches to attention-based neural machine translation, arXiv preprint arXiv:1508.04025, 2015, 11 pages.
Wu et al., Google's neural machine translation system: Bridging the gap between human and machine translation, arXiv preprint arXiv:1609.08144, 2016, 23 pages.
Chen et al., The rise of deep learning in drug discovery, Drug Discovery Today, vol. 23, No. 6, pp. 1241-1250, Jun. 2018.

Chang et al., Cancer Drug Response profile scan (CDRscan): a deep learning model that predicts drug effectiveness from cancer genomic signature, Scientific reports 8, No. 1, 2018, 11 pages.
Oskooei et al., PaccMann: Prediction of anticancer compound sensitivity with multi-modal attention-based neural networks, arXiv preprint arXiv:1811.06802, 2018, 13 pages.
Manica et al., Towards Explainable Anticancer Compound Sensitivity Prediction via Multimodal Attention-based Convolutional Encoders, ICML2019, Jun. 14, 2019, Grace Period Disclosure 11 Pages.
Manica et al., Deep learning for disease-driven drug design, https://www.meetup.com/Deep-Learning-Zurich-DLZH/events/261927228/, Jun. 25, 2019. Grace Period Disclosure 51 Pages.
Merolla et al., A Million Spiking-Neuron Integrated Circuit with a Scalable Communication Network and Interface, Science, vol. 345, Issue 6197, 2014, 7 pages.
Yang et al., Hierarchical Attention Networks for Document Classification, Proceedings of the 2016 Conference of the North American Chapter of the Association for Computational Linguistics: Human Language Technologies, pp. 1480 to 1489, 2016.
Willia, Simple Statistical Gradient-Following Algorithms for Connectionist Reinforcement Learning, Mach. Learn. 8, 229-256 (1992).
Le Tourneau et al., Treatment Algorithms Based on Tumor Molecular Profiling: The Essence of Precision Medicine Trials, JNCI Journal of the National Cancer Institute, 2016, 108(4): djv362, 10 pages.
Olivecrona et al., Molecular De-Novo Design through Deep Reinforcement Learning, Cornell University Library, Computer Science, Artificial Intelligent, arXiv:1704.07555, Apr. 25, 2017.
Seyed Ali Kazemi Oskooei et al., unpublished U.S. Appl. No. 16/413,399, filed May 15, 2019, Drug Efficacy Prediction for Treatment of Genetic Disease, pp. 1-25 plus 5 sheets of drawings.
Paul J. Otterstedt, List of IBM Patents or Patent Applications Treated as Related, Dec. 19, 2019, pp. 1-2.

DRUG COMPOUND IDENTIFICATION FOR TARGET TISSUE CELLS

CROSS REFERENCE TO A RELATED APPLICATION

This application is a continuation-in-part of U.S. application Ser. No. 16/413,399, filed on May 15, 2019, which is incorporated herein by reference in its entirety.

STATEMENT REGARDING PRIOR DISCLOSURES BY THE INVENTOR OR A JOINT INVENTOR

The following disclosures are submitted under 35 U.S.C. 102(b)(1)(A): "PaccMann: Prediction of anticancer compound sensitivity with multi-modal attention-based neural networks", Ali Oskooei, Jannis Born, Matteo Manica, Vigneshwari Subramanian, Julio Sáez-Rodriguez, Maria Rodriguez Martinez, arXiv: 1811.06802v1 [cs.LG], 16 Nov. 2018; "Towards Explainable Anticancer Compound Sensitivity Prediction via Multimodal Attention-based Convolutional Encoders", Matteo Manica, Ali Oskooei, Jannis Born, Vigneshwari Subramanian, Julio Sáez-Rodriguez, Maria Rodriguez Martinez, ICML2019, 14 Jun. 2019; and "Deep learning for disease-driven drug design", Matteo Manica, Ali Oskooei, Jannis Born, Joris Cadow, Maria Rodriguez Martinez, https://www.meetup.com/Deep-Learning-Zurich-DLZH/events/261927228/, 25 Jun. 2019.

BACKGROUND

The present invention relates generally to drug compound identification for target tissue cells. Methods are provided for identifying drug compounds having a desired biomolecular action on target tissue cells, together with apparatus and computer program products implementing such methods.

Often a disease is not one disease but rather a collection of related diseases. For example, genetic diseases such as cancer often display a collection of sub-types, whereby different patients suffering from a particular type of cancer may have different genetic mutations and, potentially, need a different course of treatment. There is strong evidence that a tumor's genetic makeup can influence the outcome of anti-cancer drug treatment resulting in heterogeneity in clinical response of various patients to a certain drug. This has led to the promise of personalized or precision medicine in which biomolecular data, such as gene expression data or other molecular biomarkers obtained from patients, may be used to design a targeted course of treatment.

With the emergence of large datasets linking biomolecular profiles to efficacy of pharmaceutical drugs, machine learning can be used to harness this data in the interests of precision medicine. Machine learning provides techniques for processing datasets from a real-word application in relation to a basic model for the application in order to train, or optimize, the model for the application in question. The model can then be applied to perform inference tasks based on new (unseen) data generated in that application.

SUMMARY

According to one aspect of the present invention there is provided a method for identifying drug compounds having a desired biomolecular action on target tissue cells. The method includes providing a reinforcement learning model comprising an agent and a critic. The critic comprises a neural network pre-trained to generate, from input biomolecular data characterizing tissue cells and input compound data defining a compound molecule, a property value for said biomolecular action of that compound molecule on those tissue cells. The agent comprises a neural network adapted to generate the aforementioned compound data in dependence on input biomolecular data. The method includes supplying biomolecular data characterizing patient tissue cells to the agent and supplying that biomolecular data, and the compound data generated therefrom by the agent, to the critic to obtain a property value for that compound data in an iterative training process in which reward values, dependent on the property values, are used to progressively train the agent to optimize the reward value for compound data generated thereby. The method further comprises, after training the agent, supplying target biomolecular data, characterizing the target tissue cells, to the agent to generate compound data corresponding to a set of drug compounds.

Respective further aspects of the invention provide a system for implementing methods for identifying drug compounds as described above, and a computer program product comprising a computer readable storage medium embodying program instructions, executable by a computing system, to cause the computing system to perform such methods.

Embodiments of the invention will be described in more detail below, by way of illustrative and non-limiting example, with reference to the accompanying drawings.

DETAILED DESCRIPTION

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Targeted drug identification methods embodying the invention may be performed as computer-implemented methods in which neural network models are implemented by software in a computing system. Other embodiments of the invention may employ neural network models implemented (wholly or partially) in hardware. Methods embodying the invention may be implemented (wholly or partially) by a computing system comprising one or more general- or special-purpose computers, each of which may comprise one or more (real or virtual) machines, providing functionality for implementing operations described herein. Steps of methods embodying the invention may be implemented by program instructions, e.g. program modules, implemented by a processing apparatus of the system. Generally, program modules may include routines, programs, objects, components, logic, data structures, and so on that perform particular tasks or implement particular abstract data types. The computing system may be implemented in a distributed computing environment, such as a cloud computing environment, where tasks are performed by remote processing devices that are linked through a communications network. In a distributed computing environment, program modules may be located in both local and remote computer system storage media including memory storage devices.

Figure 1:
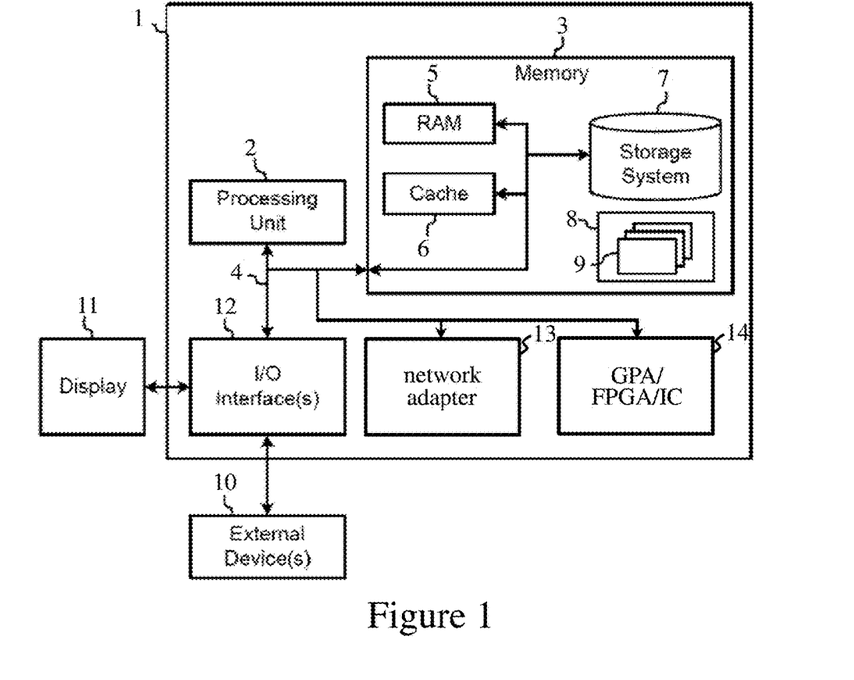
FIG. 1 is a schematic representation of a computer for implementing targeted drug identification methods embodying the invention.

FIG. 1 is a block diagram of exemplary computing apparatus for implementing methods embodying the invention. The computing apparatus is shown in the form of a general-purpose computer 1. The components of computer 1 may include processing apparatus such as one or more processors represented by processing unit 2, a system memory 3, and a bus 4 that couples various system components including system memory 3 to processing unit 2.

Bus 4 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer 1 typically includes a variety of computer readable media. Such media may be any available media that is accessible by computer 1 including volatile and non-volatile media, and removable and non-removable media. For example, system memory 3 can include computer readable media in the form of volatile memory, such as random access memory (RAM) 5 and/or cache memory 6. Computer 1 may further include other removable/non-removable, volatile/non-volatile computer system storage media. By way of example only, storage system 7 can be provided for reading from and writing to a non-removable, non-volatile magnetic medium (commonly called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can also be provided. In such instances, each can be connected to bus 4 by one or more data media interfaces.

Memory 3 may include at least one program product having one or more program modules that are configured to carry out functions of embodiments of the invention. By way of example, program/utility 8, having a set (at least one) of program modules 9, may be stored in memory 3, as well as an operating system, one or more application programs, other program modules, and program data. Each of the operating system, one or more application programs, other program modules, and program data, or some combination thereof, may include an implementation of a networking environment. Program modules 9 generally carry out the functions and/or methodologies of embodiments of the invention as described herein.

Computer 1 may also communicate with: one or more external devices 10 such as a keyboard, a pointing device, a display 11, etc.; one or more devices that enable a user to interact with computer 1; and/or any devices (e.g., network card, modem, etc.) that enable computer 1 to communicate with one or more other computing devices. Such communication can occur via Input/Output (I/O) interfaces 12. Also, computer 1 can communicate with one or more networks such as a local area network (LAN), a general wide area network (WAN), and/or a public network (e.g., the Internet) via network adapter 13. As depicted, network adapter 13 communicates with the other components of computer 1 via bus 4. Computer 1 may also communicate with additional processing apparatus 14, such as one or more GPUs (graphics processing units), FPGAs, and/or integrated circuits (ICs) for implementing embodiments of the invention. In general, such additional processing apparatus may be internal or external to computer 1. It should be understood that although not shown, other hardware and/or software components could be used in conjunction with computer 1. Examples include, but are not limited to: microcode, device drivers, redundant processing units, external disk drive arrays, RAID systems, tape drives, and data archival storage systems, etc.

Embodiments described below exploit machine learning models based on neural networks. Neural network models perform computational tasks in a manner inspired by biological architectures of the nervous system. These models are based on a fundamental principle of biological systems whereby neurons are interconnected via synapses which relay weighted signals between the neurons. Neural network architectures exploit a logical construction in which a series of layers of neurons are interconnected so that output signals of neurons in one layer are weighted and transmitted to neurons in the next layer. Each neuron in a given layer can be connected to one or more neurons in another layer, and different weights can be associated with respective neuron-neuron connections. Each neuron generates output signals dependent on its accumulated inputs, whereby weighted signals can be propagated over layers of the network. The sets of weights associated with the various layers of a neural network are learned during a model training operation. The weights are trained via an iterative process in which the network is exposed to a set of training data and the weights are repeatedly updated as the network "learns" from the training data. Training involves an iterative cycle of signal propagation and weight-update operations, with the network weights being progressively updated until a convergence condition is achieved. The resulting trained network model, with the trained (optimized) weights defined via this process, can then be applied for inference.

Figure 2:
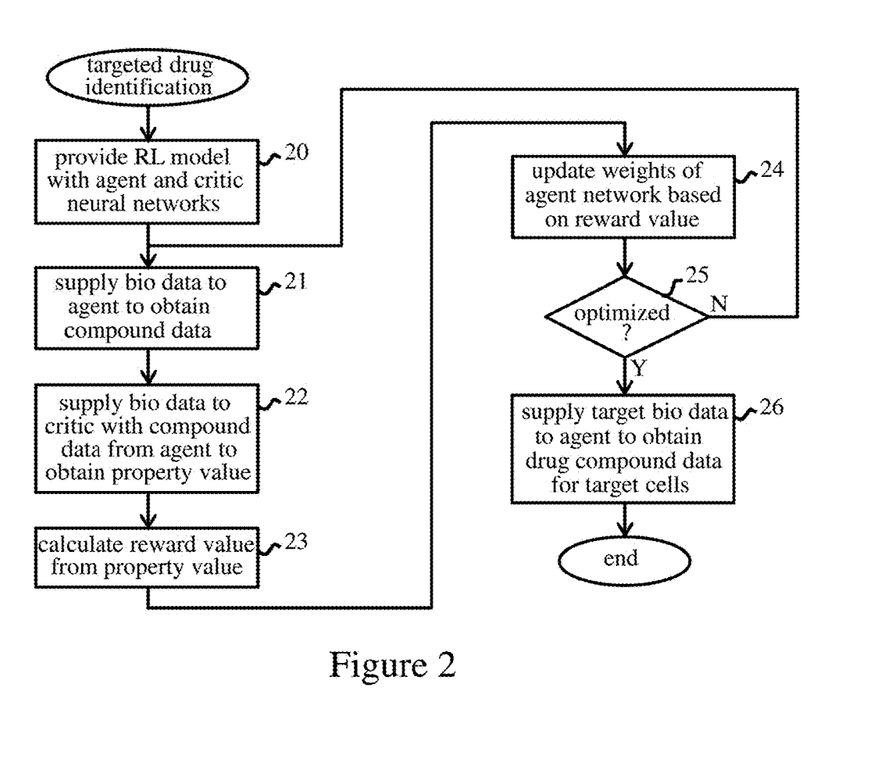
FIG. 2 indicates steps of a targeted drug identification method embodying the invention.
Figure 3:
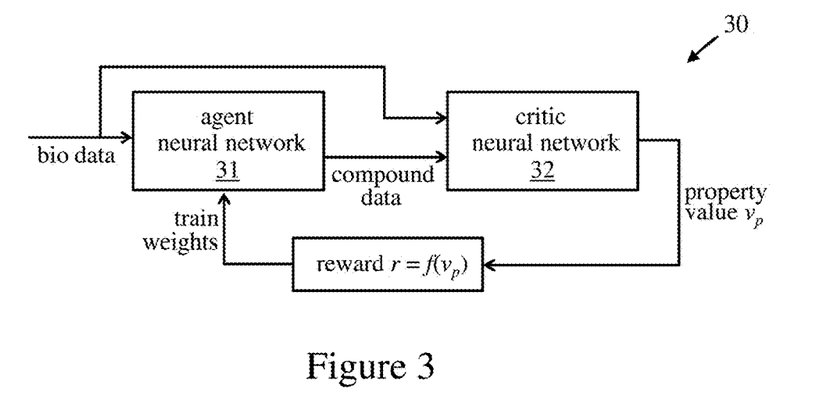
FIG. 3 is a schematic representation of a reinforcement learning model used in the FIG. 2 method.

FIG. 2 indicates basic steps of a method embodying the invention for identifying drug compounds having a desired biomolecular action on target tissue cells. The method employs a reinforcement learning model which is implemented in step 20 of FIG. 2. The basic architecture of this model is shown in FIG. 3. The model 30 comprises an agent 31 and a critic 32 which are interconnected in a reinforcement learning architecture. The critic 32 comprises a neural network which is pre-trained to generate, from input biomolecular ("bio") data characterizing tissue cells and input compound data defining a compound molecule, a property value $v_p$ for the desired biomolecular action of that compound molecule on those tissue cells. The agent 31 comprises a neural network which is adapted to generate the aforementioned compound data in dependence on input biomolecular data. The resulting compound data is thus conditioned on the input biomolecular data. The model 30 is trained via an iterative training process indicated in steps 21 to 25 of FIG. 2. In step 21, computing system 1 supplies biomolecular data characterizing patient tissue cells to the agent 31 to obtain compound data for a compound molecule. In step 22, system 1 supplies the biomolecular data supplied to the agent in step 21, and the compound data generated therefrom by the agent, to the critic 32 to obtain a property value $v_p$ for that compound data. In step 23, system 1 calculates a reward value r, dependent on the property value $v_p$, for the compound data generated by the agent in the current iteration. In step 24, system 1 updates the network weights of agent 31 in dependence on the reward value r so as to progress towards a more optimal state (producing higher reward values). In step 25, system 1 checks whether a convergence condition, indicating optimized weights in agent 31, has been achieved. If not ("N" at decision step 25), operation reverts to step 21 for a further iteration of the training operation. Steps 21 to 25 thus implement an iterative training process in which reward values, dependent on the property values $v_p$, are used to progressively train the agent 31 to optimize the reward value for compound data generated thereby.

When the agent network weights have been optimized ("Y" at decision step 25), the agent is fully trained and can be applied for inference without further feedback from critic 32. After training the agent, system 1 supplies target biomolecular data, characterizing the target tissue cells, to the agent to generate compound data corresponding to a set of drug compounds. Compound data may be obtained here for a set of one or more drug compounds, with compound data for a plurality of drugs being obtained by iteratively supplying target bio data to the agent or by otherwise controlling agent operation as explained below.

The compound data generated in step 26 defines compound molecules for one or more potential drug compounds having the desired biomolecular action on the specific tissue cells characterised by the target biomolecular data. The above method thus provides an elegant and efficient technique for identification of targeted pharmaceutical drugs. While the results may suggest existing drug compounds which would be efficacious for a target cell profile, the method also provides de novo design of pharmaceutical drugs for particular cell profiles. Moreover, unlike prior techniques which focus solely on chemical properties and structure of molecules in the compound generation process, embodiments of the invention adopt a multimodal approach, generating compounds using both chemical structure information and a biomolecular characterization of the tissue where the molecule is applied. By accommodating the environment in which a drug has to be effective, embodiments of the invention provide a more effective, holistic approach to drug identification/design, offering a significant advance in precision medicine.

The aforementioned biomolecular action may comprise any desired therapeutic/prophylactic effect, or set of effects, on cell lines. Property values generated by the critic may comprise any property characterizing the action of the compound molecule on the tissue cells. For example, a property value may comprise an efficacy value indicating efficacy of the compound molecule in producing the desired action. Such property/efficacy values may be expressed in a variety of ways. In embodiments below, for example, drug efficacy is expressed in terms of $IC_{50}$ values which indicate drug concentration required to achieve 50% of the drug's maximum inhibitory effect. While $IC_{50}$ values are widely used as a measure of drug efficacy, in general any measurement values indicating sensitivity of biomolecular processes to a drug may be used as property values. Reward values may comprise the raw property values per se or another function f thereof, and particular examples are given below.

Biomolecular data characterizing cells may comprise, for instance: gene expression data, e.g. microarray or RNASeq (Ribonucleic Acid Sequencing) measurements; protein expression data, e.g. RPPA (Reverse Phase Protein Array) or SWATH-MS (Sequential Windowed Acquisition of All Theoretical Fragment Ion Mass Spectra) measurements; genomics, e.g. SNV (Single Nucleotide Variant) or CNA (Circulating Nucleic Acids) measurements; or, in general, one or a combination of any type of biomolecular measurements representing a cell-sample.

In preferred embodiments below, the compound data defining a compound molecule comprises a string representation of the molecule. String representations, such as SMILES (Simplified Molecular-Input Line-Entry System) strings and SMARTS (SMILES Arbitrary Target Specification) strings, are well-known line notations for representing the chemical structure of a molecule in a raw form. These raw data strings are distinct from other representations, such as fingerprints or chemical descriptors, which are based on engineered features that describe the chemical properties and structure of a compound. In general, however, compound data may comprise any data representation of a compound molecule, including strings, fingerprints, graphs and chemical descriptors.

The biomolecular data used to train agent 31 may be obtained or produced from a dataset (stored locally or accessed remotely by system 1) of biomolecular measurements on cell-lines of patients, e.g. from patient tumors. Training may be based on patient profiles for multiple patients with a particular disease, disease-type or category of diseases according to required generality of the trained model. The agent may be trained for individual patient profiles in succession. The agent may generate molecules via a step-by-step process, e.g. character-by-character for string representations, with cumulative reward values being generated from property values produced at each step. For efficiency, however, the agent generates compound data for a complete molecule in preferred embodiments, with property/reward values being generated for the resulting molecule.

In general, the agent and critic neural networks may be implemented in hardware or software or a combination thereof. Various implementations for neurons and synapses are known in the art, including circuits which exploit memristive properties of nanodevices, e.g. resistive memory cells such as phase-change memory (PCM) cells. Dense cross-bar arrays of such memristive devices offer massively parallel and highly area- and energy-efficient neural networks. Neural network architectures can be efficiently implemented in integrated circuits (see, for example, "A Million Spiking-Neuron Integrated Circuit with a Scalable Communication Network and Interface", Merolla et al., Science, Vol. 345, Issue 6197, 2014). Memristive devices based on resistive RAM (RRAM, or ReRAM) cells including conductive bridge RRAM cells, oxide or metal-oxide RRAM cells, and carbon RRAM cells may also be employed for neuron/synapse implementation. In general, neurons/synapses can be implemented in any desired manner with particular network functionality provided by hardware and/or software.

Network training can employ a variety of well-known techniques in which weight updates are calculated in order maximize/minimize some predefined function of the reward values. In general, network weights may be updated after every iteration, or after accumulating weight-updates calculated over a set of iterations for a batch of input bio data examples. Convergence (optimization) conditions can be defined in various ways, e.g. as the point at which no further improvement is achieved, or improvement is less than some threshold value, and the particular convergence condition is orthogonal to the operation described herein.

Figure 4:
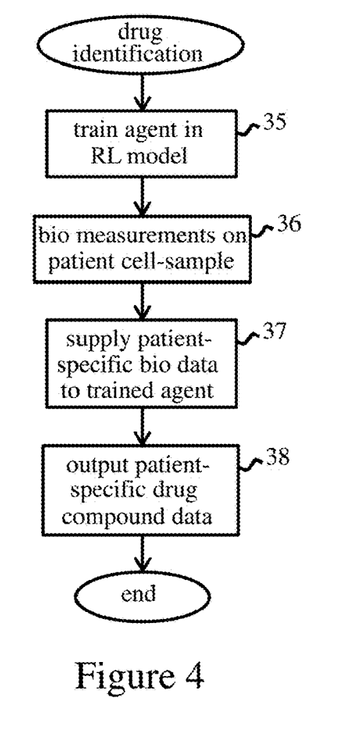
FIG. 4 indicates steps of a patient-specific drug identification method embodying the invention.

FIG. 4 indicates steps of a method for identifying drugs targeted to a particular patient. Step 35 represents the agent training process of steps 20 to 25 of FIG. 2. The agent may be trained here using biomolecular data profiling disease-cell samples of patients with the same disease or disease sub-type as the target patient. In step 36, biomolecular measurements are made on a disease-cell sample from the target patient to obtain patient-specific biomolecular data. For a patient suspected to suffer from a certain type of cancer, for example, tumor biopsy is generally performed and analysed to obtain the biomolecular data. In step 37, the patient-specific biomolecular data is supplied to the trained agent as the target biomolecular data. In step 38, the resulting patient-specific drug compound data is output for use in personalized treatment planning for the patient. For example, the output compounds may be used to match existing drug compounds to the patient for selecting the most appropriate treatment, or even identify a new drug compound as potentially efficacious for that patient.

Figure 5:
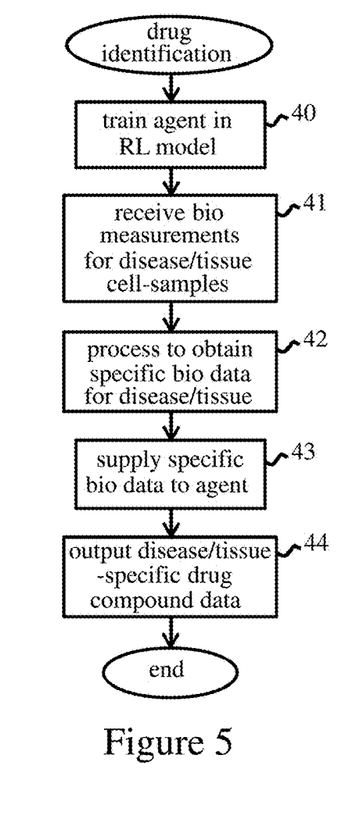
FIG. 5 indicates steps of disease/tissue-specific drug identification methods embodying the invention.

Methods embodying the invention may also be used to identify drugs targeted for action on a particular disease or tissue type. FIG. 5 indicates steps of such a method. Step 40 represents the agent training process. Training may be performed here using biomolecular data from multiple disease/tissue-cell samples for the target disease/tissue or a range of disease/tissue types according to the desired generality of the model. In step 41, biomolecular measurements for a plurality of cell-samples for the target disease/tissue are stored in system 1. In step 42, the system processes these measurements to obtain disease/tissue-specific bio data for the target disease/tissue. For example, biomolecular measurements from patients with the same (target) disease can be processed to extract common features, or average bio measurements, to obtain disease-specific bio data. Similarly, measurements of a plurality of cell-samples from like (target) tissue of different patients can be processed to extract common/average measurements to obtain tissue-specific bio data. In step 43, the disease/tissue-specific bio data is supplied to the agent as said target biomolecular data, and the resulting targeted compound data is output in step 44. The output here can be used to design new or improved treatments for the target disease or tissue type. For example, molecules generated by the agent may correspond to new compounds not previously used in treatment of the disease/tissue in question, offering de novo design of new drug compounds for precision medicine. The most promising, e.g. the most easily synthesizable, candidates may then be selected for synthesis and further analysis.

Figure 6:
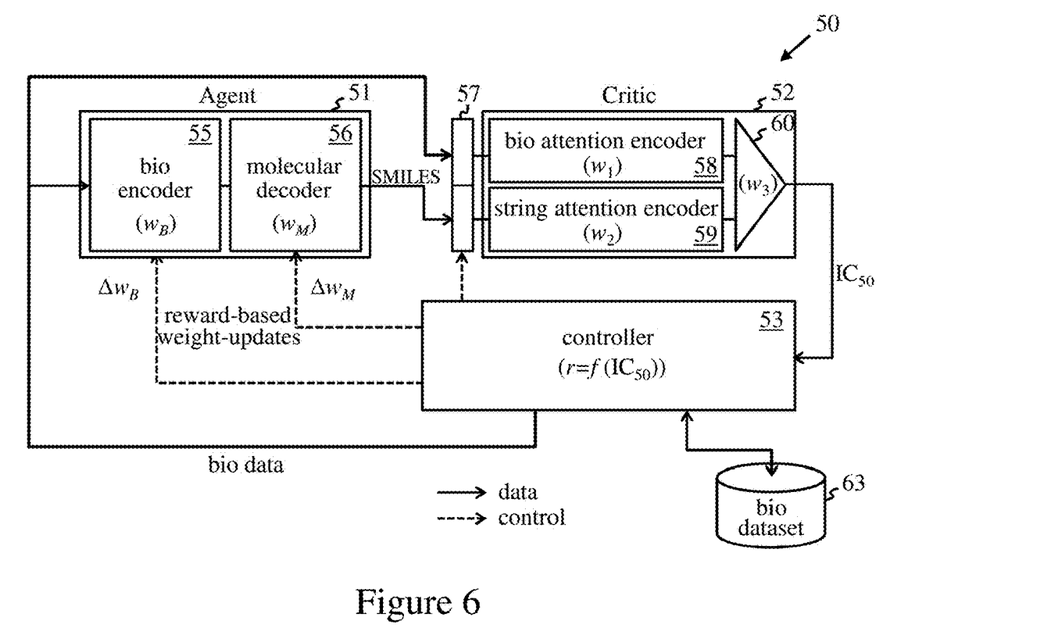
FIG. 6 is a schematic representation of a system embodying the invention for identification of targeted drug compounds.

An exemplary embodiment of the invention is described in more detail below in the context of drug identification for treatment of cancer. FIG. 6 illustrates the drug identification system and model architecture of this embodiment. The system 50 comprises an agent 51 and critic 52 configured as a deep reinforcement learning model. Control logic, indicated as controller 53, controls operation of system 30 in the training and inference processes. Particular controller functionality may be implemented by one or a combination of hardware and software, and suitable implementations will be apparent to those skilled in the art from the operation described herein. Agent 51 comprises a deep neural network constructed from a bio encoder 55 and a molecular decoder 56. Bio encoder 55 comprises an encoder network with pre-trained weights $w_B$. This encoder network is pre-trained in an autoencoder architecture for biomolecular data, characterizing patient tissue cells, as described below. Molecular decoder 56 comprises a decoder network with pre-trained weights $w_M$. This decoder network is pre-trained in an autoencoder architecture for compound data, here SMILES strings, as described below. The output of the bio encoder 55 is operatively coupled to the input of molecular decoder 56 as explained below.

Critic neural network 52 comprises a deep neural network which receives a data pair, indicated at 57, comprising a SMILES string output by agent 51 and bio data supplied by controller 53. The critic 52 comprises a first attention-based encoder (bio attention encoder 58) with pre-trained weights $w_1$ for encoding the bio data of an input data pair to produce encoded bio data. The critic includes a second attention-based encoder (string attention encoder 59) with pre-trained weights $w_2$ for encoding the string data of an input data pair to produce encoded compound data. The critic has a final set of dense layers 60, with pre-trained weights $w_3$, for processing the encoded bio and compound data from attention encoders 58 and 59 to produce an efficacy value, here an $IC_{50}$ value.

Figure 7A:
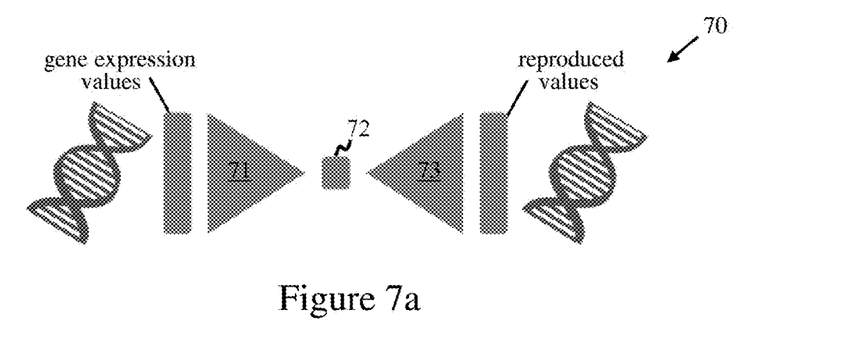
FIGS. 7*a* and 7*b* illustrate autoencoder architectures used to construct an agent in the FIG. 6 system.
Figure 7B:
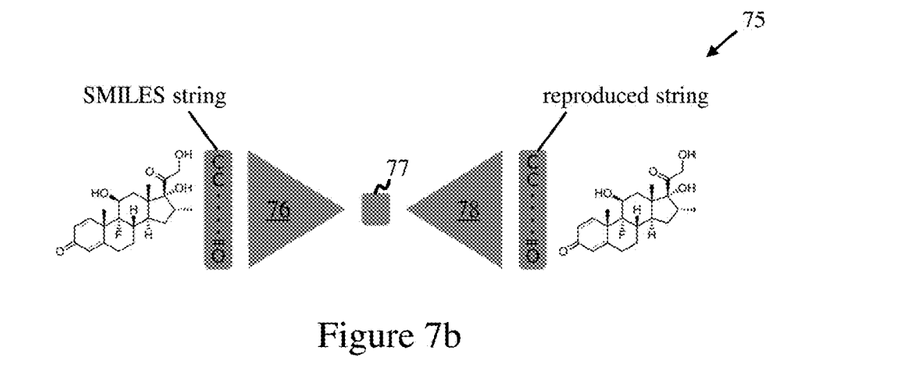

Bio encoder 55 and molecular decoder 56 of the agent are trained in respective autoencoder architectures indicated schematically in FIGS. 7a and 7b. FIG. 7a illustrates the training architecture for the bio encoder 55. In this example, the bio encoder is trained in a variational autoencoder architecture for gene expression data of cancer cells. Such gene expression data comprises gene expression values corresponding to measurements relating to the individual genes, and in particular the functional products of these genes, in a cell sample. Typically, gene expression data comprises relative (with respect to a control sample) mRNA abundance measurements for mRNAs transcribing genes within a cell. Variational autoencoders are well known in the art and need not be described in detail here. Briefly, however, the bio autoencoder 70 of FIG. 7a comprises an encoder network 71 having a series of network layers which encode the input gene expression values for a sample into the parameters of a distribution (e.g. a Gaussian, mean and variance) that can be used to sample points in a latent space, indicated at 72, with reduced dimensions compared to the network input. The output of encoder 71 in this space is used to sample a point in latent space 72 that is then supplied as the input to a decoder network 73 which produces an output corresponding to the original input of encoder 71. Bio variational autoencoder 70 can be trained from a dataset of gene expression data for cancer cell-lines, e.g. from the GDSC (Genomics of Drug Sensitivity in Cancer) dataset. Training involves a supervised learning process to optimize weights of encoder 71 and decoder 73 so that the decoder output resembles the encoder input as closely as possible.

FIG. 7b shows a similar autoencoder architecture for molecular strings which is implemented here as a variational autoencoder based on RNN (recurrent neural network) layers. The variational autoencoder 75 receives SMILES strings which are encoded by an encoder neural network 76. The encoder output is used to sample a point in latent space 77. This is then supplied to decoder neural network 78 which attempts to reconstruct the original input string. Training here uses a dataset of molecular strings to optimize the network weights via a supervised learning process for optimal reconstruction of input strings.

Figure 8:
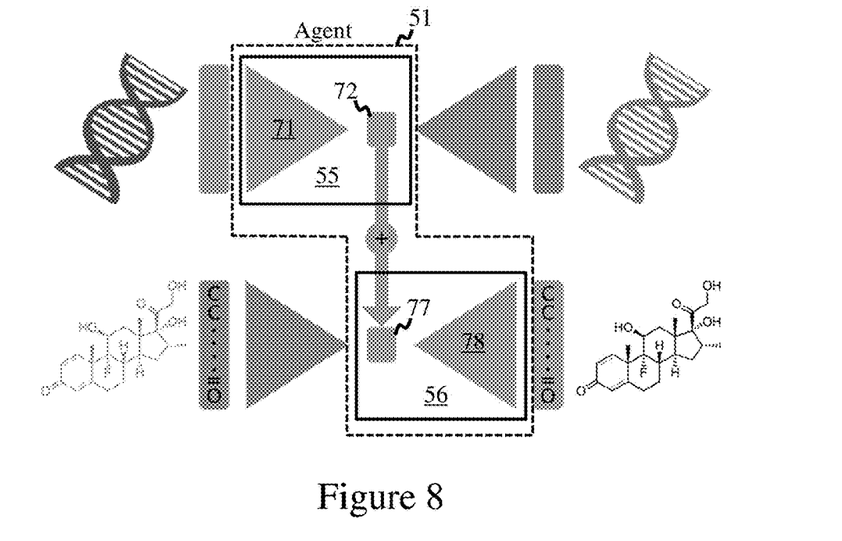
FIG. 8 illustrates architecture of the agent in the FIG. 6 system.

After training, the agent 51 of system 50 is constructed as shown in FIG. 8 from the encoder 71 of bio variational autoencoder 70 and the decoder 78 of molecular variational autoencoder 75. An output of bio encoder 55 is used to sample a point in latent space 72. This is then mapped to a point in latent space 77 of molecular decoder 56 via a mapping function, in this example by addition of the bio output point in latent space 72 to the origin (zero input) in latent space 77.

Attention-based encoders, as employed in critic 52, are well-known in the machine learning field. Briefly, attention-based encoders are implemented by neural network structures which project the input into an attention space and distribute attention over different parts of the input, according to different weights which determine the degree of importance attached to the various parts of the input. These attention weights, denoted by vectors $\alpha$ and $\beta$ below, are learned during training of weights $w_1$ to $w_3$ of the critic and are used to comparatively weigh different features of the inputs in encoders 58 and 59 according to their relative contribution in making a better overall efficacy prediction. The inputs to encoders 58 and 59 are masked using these attention weights and the masked feature sets are paired and fed to final network layers 60.

Figure 9:
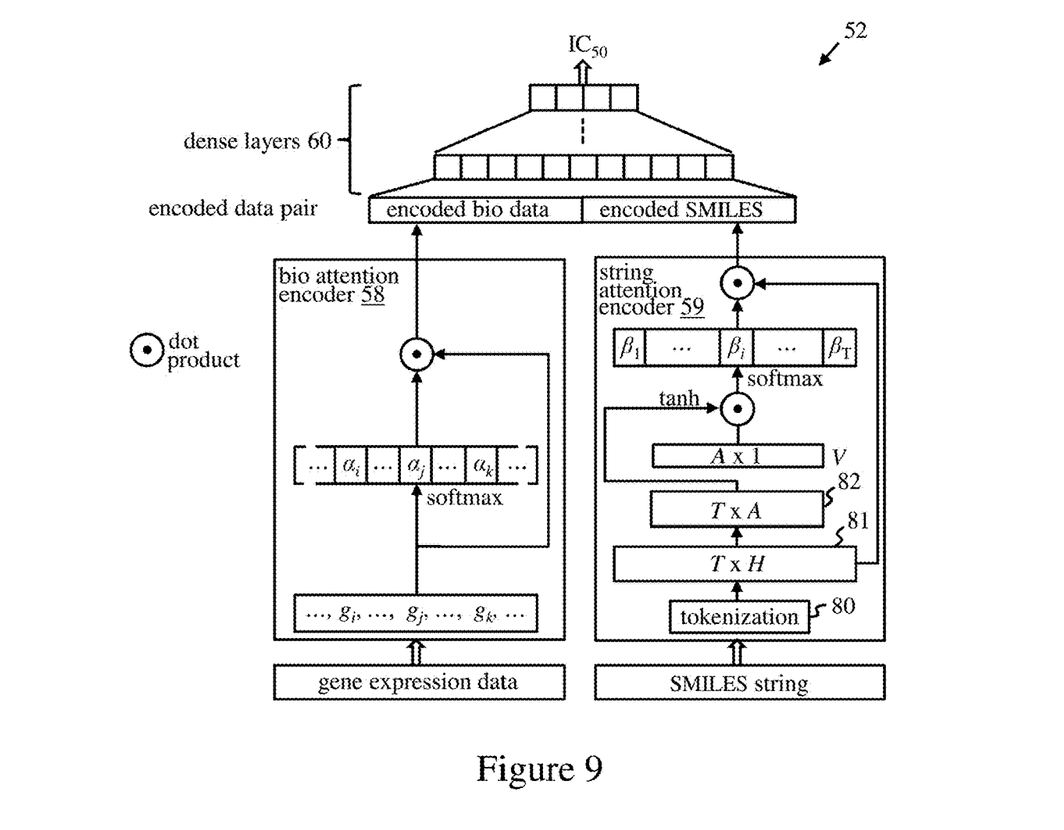
FIG. 9 illustrates architecture of a critic in the FIG. 6 system.
Figure 10:
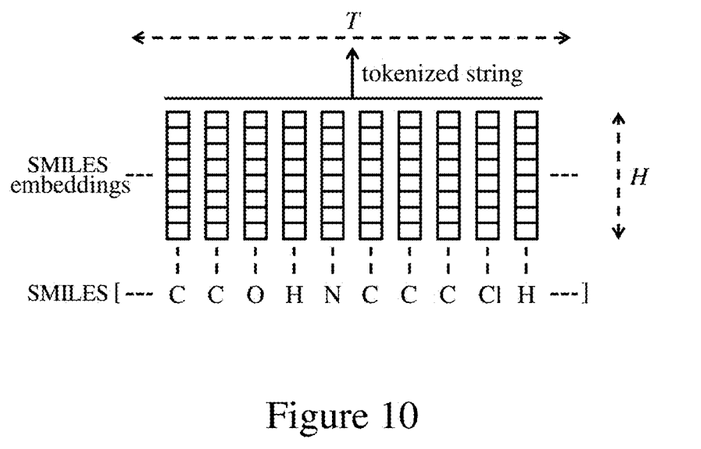
FIG. 10 illustrates a tokenization operation performed in the FIG. 9 architecture.

FIG. 9 shows an exemplary implementation of critic 52 in more detail. Bio attention encoder 58 comprises a softmax layer which produces individual attention weights $\alpha_i$ (of vector $\alpha$) for respective gene expression values $g_i$ in the input bio data, ensuring that the most informative genes receive a higher weight. The attention weights $\alpha_i$ are applied to the gene expression values $g_i$ in a dot product to produce the encoded bio data. String attention encoder 59 is based on an attention mechanism originally developed for document classification and here adapted to SMILES representations (see "Hierarchical Attention Networks for Document Classification", Zichao Yang et al., Proceedings of the 2016 Conference of the North American Chapter of the Association for Computational Linguistics: Human Language Technologies, pp. 1480 to 489, 2016;). The encoder 59 includes an initial tokenization stage 80 which tokenizes the input SMILES string as illustrated schematically in FIG. 10. An embedding layer of tokenization stage 80 transforms the raw SMILES strings into a sequence of vectors in an embedding space. The SMILES sequences are tokenized using a regular expression to ensure charged or multi-character atoms (e.g., Cl or Br) are added as distinct tokens to the dictionary. The resulting atomic sequences of length T are represented as $E=\{e_1, \ldots, e_T\}$ with learned embedding vectors $e_i$ of length H for each dictionary token. The resulting tokenized strings (SMILES embeddings) of FIG. 10 correspond to block 81 of FIG. 9. The tokenized strings are then transformed into an attention space 82 of dimensions T×A. A learned vector V is combined with the atom annotations from the attention space through a dot product, the output of which is fed to a softmax layer which produces the vector $\beta$ of SMILES attention weights $\beta_i$. The input tokens are filtered with the attention weights, via a further dot product, to produce a single vector of hidden dimensionality H. The attention weights $\beta_i$ were computed as:

$$\beta_i = \frac{\exp(u_i)}{\Sigma_j^T u_j} \text{ where } u_i = V^T \tanh(W_e e_i + b)$$

where the matrix $W_e \in \mathbb{R}^{A \times H}$ and the bias vector $b \in \mathbb{R}^{A \times 1}$ are learned in a dense layer. The encoded data pair, comprising the encoded bio and compound data from attention encoders 58 and 59, is supplied to a final set of dense feedforward layers 60 to produce the output $IC_{50}$ value.

The weights $w_1$ to $w_3$, including attention weights $\alpha$ and $\beta$, of critic 52 are learned during a training process which uses a dataset correlating biomolecular data for patient cell-samples with drug efficacy values for a plurality of drug compounds. For example, gene expression and drug $IC_{50}$ data from the GDSC dataset can be employed for training. Training involves defining from this dataset a set of training data pairs, each comprising bio data (here gene expression data) for a cell-sample and a SMILES string for a drug whose efficacy value for that cell-sample is given in the dataset. For each training pair, the bio data is supplied to bio-attention encoder 58 and the SMILES string is supplied to string attention encoder 59, and the corresponding $IC_{50}$ values are used as labels in a supervised learning process to train the critic to generate $IC_{50}$ values corresponding (as closely as possible) to the labels.

Figure 11:
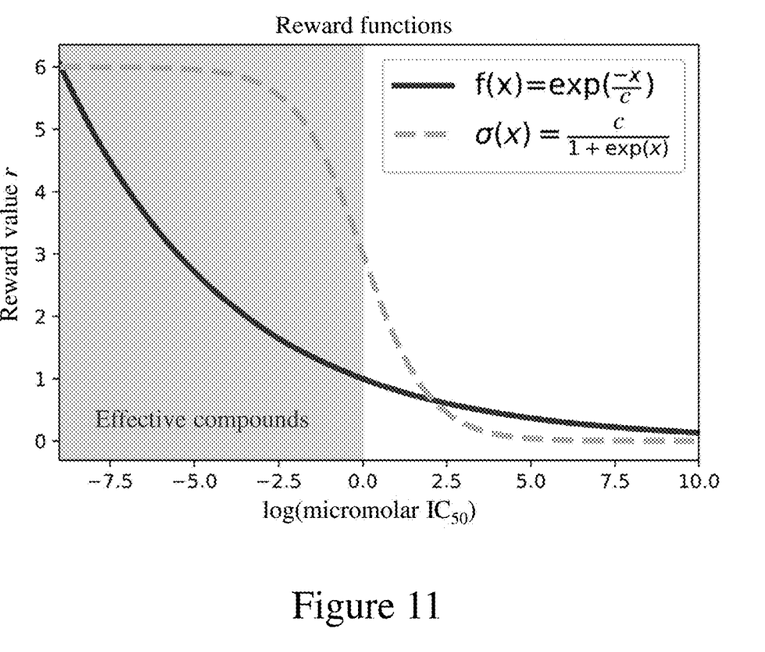
FIG. 11 illustrates reward functions for use in the FIG. 6 system.

Operation of system 50 involves further training of the weights $w_B$ and $w_M$ of agent 51 in the reinforcement learning architecture. Controller 53 extracts bio profiles for cell-lines from a bio dataset 63 such as the GDSC dataset. Controller 53 supplies each bio profile to agent 51, and supplies that bio profile, together with the resulting SMILES string generated by the agent, in a data pair 57 to critic 52. The $IC_{50}$ value produced by the critic for the data pair is received by controller 53 which calculates a reward value $r=f(IC_{50})$ for the molecule generated by the agent. Controller 53 then calculates weight-updates $\Delta w_B$ and $\Delta w_M$ for respective weights $w_B$ and $w_M$ of the agent. Weight-updates can be calculated in generally known manner based on a variety of training algorithms. In this example, weight updates are calculated using a REINFORCE algorithm (see, e.g., "Simple Statistical Gradient-Following Algorithms for Connectionist Reinforcement Learning", R. J. Willia, Mach. Learn. 8, 229-256 (1992)) and backpropagation of gradients in agent network 52 for the reward value for the current iteration. The training process iterates for successive training examples, with the agent weights being progressively updated to improve the reward values for the generated molecules. In this operation, reward values can be calculated in controller 53 using any function which correlates reward with improved drug efficacy. FIG. 11 shows exemplary reward functions, here an exponential function $r=f(x)$ and a sigmoid function $r=\sigma(x)$ where $x=\log(\text{micromolar } IC_{50})$ and c is a constant.

After training the agent, controller 53 can use the agent for inference based on target bio data, e.g. as described with reference to FIGS. 4 and 5. For a given target bio profile, controller 53 preferably controls agent 52 to generate a plurality of compound molecules. This may be achieved by iteratively supplying the target profile to the agent and relying on inherent stochasticity of the agent neural network to generate a set of candidate molecules for the target profile. Alternatively, controller 53 may supply the target profile once to agent 51, and then sample multiple points around the resulting output point in the latent space of the bio encoder output. The sampled points can then be used for molecule generation in molecular decoder 56.

It will be appreciated that numerous changes and modifications can be made to the exemplary embodiments described. For example, other autoencoder architectures may be used in agent 51. The agent can also be implemented using various other generative models for molecules, such as GANs (Generative Adversarial Networks) or Seq2seq (Sequence-to-Sequence) networks. Other mapping functions may be employed between the agent bio encoder and molecular decoder, and this mapping may be implemented by an additional neural network in some embodiments. Various other encoder architectures may also be employed in the critic. Such encoders may include additional processing stages, such as initial recurrent or convolutional neural network layers. Some embodiments may employ a multi-channel configuration of encoders in the critic such that encoders in different channels focus on different features of a molecule for instance.

Methods embodying the invention may of course be applied to diseases other than cancer, including other multifactorial genetic diseases displaying different subtypes due to different genetic mutations such as cardiovascular disease and Alzheimer disease.

In general, where features are described herein with reference to a method embodying the invention, corresponding features may be provided in a system/computer program product embodying the invention, and vice versa.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for identifying and synthesizing drug compounds having a desired biomolecular action on target tissue cells, the method comprising:
   providing a reinforcement learning model comprising an agent and a critic, wherein the critic comprises a neural network pre-trained to generate, from input biomolecular data characterizing tissue cells and input compound data defining a compound molecule, a property value for said biomolecular action of that compound molecule on those tissue cells, and wherein the agent comprises a neural network adapted to generate said compound data in dependence on input biomolecular data;
   supplying biomolecular data characterizing patient tissue cells to the agent and supplying that biomolecular data, and the compound data generated therefrom by the agent, to the critic to obtain a property value for that compound data in an iterative training process in which reward values, dependent on the property values, are used to progressively train the agent to optimize the reward value for compound data generated thereby;
   after training the agent, supplying target biomolecular data, characterizing said target tissue cells, to the agent to generate compound data corresponding to a set of drug compounds; and
   synthesizing a drug compound selected from the set of drug compounds.

2. A method as claimed in claim 1 wherein the agent neural network comprises an encoder network which is pre-trained in an autoencoder architecture for biomolecular data characterizing patient tissue cells, and a decoder network which is pre-trained in an autoencoder architecture for said compound data for compound molecules, an output of said encoder network being operatively coupled to an input of said decoder network.

3. A method as claimed in claim 2 including training the encoder and decoder networks in the respective autoencoder architectures.

4. A method as claimed in claim 2 wherein each of said autoencoder architectures comprises a variational autoencoder.

5. A method as claimed in claim 1 wherein the critic neural network comprises a first attention-based encoder for encoding the input biomolecular data to produce encoded biomolecular data, a second attention-based encoder for encoding the input compound data to produce encoded compound data, and a set of dense layers for processing the encoded biomolecular and compound data to produce said property value.

6. A method as claimed in claim 5 including training the critic neural network, using
   a dataset correlating biomolecular data for patient cell-samples with drug efficacy values for said biomolecular action of a plurality drug compounds, by:
   defining training data pairs each comprising biomolecular data for a said cell-sample and said compound data for a said drug;
   supplying the biomolecular data of each training pair to the first attention-based encoder and the compound data of that pair to the second attention-based encoder, and performing a supervised learning process to train the critic neural network to generate property values corresponding to said drug efficacy values for the training pairs.

7. A method as claimed in claim 1 wherein said compound data comprises a string representation of a compound molecule.

8. A method as claimed in claim 1 wherein said biomolecular data comprises gene expression data.

9. A method as claimed in claim 1 including:
   making biomolecular measurements on a patient cell-sample to obtain patient-specific biomolecular data; and
   supplying the patient-specific biomolecular data to the agent as said target biomolecular data.

10. A method as claimed in claim 1 including:
    processing biomolecular measurements of a plurality of cell-samples from patients with the same disease to obtain disease-specific biomolecular data; and
    supplying the disease-specific biomolecular data to the agent as said target biomolecular data.

11. A method as claimed in claim 1 including:
    processing biomolecular measurements of a plurality of cell-samples from like tissue of different patients to obtain tissue-specific biomolecular data; and
    supplying the tissue-specific biomolecular data to the agent as said target biomolecular data.

12. A method as claimed in claim 1, further comprising administering, to a patient who provided the patient tissue cells, the drug selected from the set of drug compounds.

13. A system for identifying drug compounds having a desired biomolecular action on target tissue cells, the system comprising:
    a reinforcement learning model comprising an agent and a critic, wherein the critic comprises a neural network pre-trained to generate, from input biomolecular data characterizing tissue cells and input compound data defining a compound molecule, a property value for said biomolecular action of that compound molecule on those tissue cells, and wherein the agent comprises a neural network adapted to generate said compound data in dependence on input biomolecular data; and
    control logic adapted to supply biomolecular data characterizing patient tissue cells to the agent and supply that biomolecular data, and the compound data generated therefrom by the agent, to the critic to obtain a property value for that compound data in an iterative training process in which reward values, dependent on the property values, are used to progressively train the agent to optimize the reward value for compound data generated thereby;

wherein the control logic is further adapted, in response to receipt of target biomolecular data characterizing said target tissue cells after training the agent, to supply the target biomolecular data to the agent to generate compound data corresponding to a set of drug compounds.

14. A system as claimed in claim 13 wherein the agent neural network comprises an encoder network which is pre-trained in an autoencoder architecture for biomolecular data characterizing patient tissue cells, and a decoder network which is pre-trained in an autoencoder architecture for said compound data for compound molecules, an output of said encoder network being operatively coupled to an input of said decoder network.

15. A system as claimed in claim 14 wherein each of said autoencoder architectures comprises a variational autoencoder.

16. A system as claimed in claim 14 wherein the critic neural network comprises a first attention-based encoder for encoding the input biomolecular data to produce encoded biomolecular data, a second attention-based encoder for encoding the input compound data to produce encoded compound data, and a set of dense layers for processing the encoded biomolecular and compound data to produce said property value.

17. A system as claimed in claim 13 wherein said compound data comprises a string representation of a compound molecule.

18. A computer program product for identifying drug compounds having a desired biomolecular action on target tissue cells, said computer program product comprising a computer readable storage medium having program instructions embodied therein, the program instructions being executable by a computing system to cause the computing system to:

implement a reinforcement learning model comprising an agent and a critic, wherein the critic comprises a neural network pre-trained to generate, from input biomolecular data characterizing tissue cells and input compound data defining a compound molecule, a property value for said biomolecular action of that compound molecule on those tissue cells, and wherein the agent comprises a neural network adapted to generate said compound data in dependence on input biomolecular data;

supply biomolecular data characterizing patient tissue cells to the agent and supply that biomolecular data, and the compound data generated therefrom by the agent, to the critic to obtain a property value for that compound data in an iterative training process in which reward values, dependent on the property values, are used to progressively train the agent to optimize the reward value for compound data generated thereby; and after training the agent, to supply target biomolecular data, characterizing said target tissue cells, to the agent to generate compound data corresponding to a set of drug compounds.

19. A computer program product as claimed in claim 18, said program instructions being executable such that the agent neural network comprises an encoder network which is pre-trained in an autoencoder architecture for biomolecular data characterizing patient tissue cells, and a decoder network which is pre-trained in an autoencoder architecture for said compound data for compound molecules, an output of said encoder network being operatively coupled to an input of said decoder network.

20. A computer program product as claimed in claim 18, said program instructions being executable such that the critic neural network comprises a first attention-based encoder for encoding the input biomolecular data to produce encoded biomolecular data, a second attention-based encoder for encoding the input compound data to produce encoded compound data, and a set of dense layers for processing the encoded biomolecular and compound data to produce said property value.

21. A computer program product as claimed in claim 18, said program instructions being executable such that said compound data comprises a string representation of a compound molecule.

* * * * *